United States Patent
Posse et al.

(10) Patent No.: US 6,311,301 B1
(45) Date of Patent: Oct. 30, 2001

(54) SYSTEM FOR EFFICIENT UTILIZATION OF MULTIPLE TEST SYSTEMS

(76) Inventors: Kenneth E. Posse, 6626 Majestic Dr., Fort Collins, CO (US) 80528; Stig Oresjo, 2217 Scotch Pine Ct., Loveland, CO (US) 80538; Patricia Monterio, 2713 Antelope Rd., Fort Collins, CO (US) 80525; Anne Dudfield, 2301 Moss Rose La., Fort Collins, CO (US) 80526

( * ) Notice: Subject to any disclaimer, the term of this patent is extended or adjusted under 35 U.S.C. 154(b) by 0 days.

(21) Appl. No.: 09/258,632

(22) Filed: Feb. 26, 1999

(51) Int. Cl.[7] .................................................. G06F 11/00
(52) U.S. Cl. ............................................. 714/724; 714/734
(58) Field of Search ................................. 714/724, 734; 324/73.1

(56) References Cited

U.S. PATENT DOCUMENTS 4,556,840 * 12/1985 Russell ................................. 324/73.1
4,718,064 * 1/1988 Edwards et al. .

OTHER PUBLICATIONS

"Test Development Tools, Chapter 2—HP Board Consultant", pp. 2.1–2.32 and "Test Methods: Limited Access, HP Access Consultant", pp. 2.1–2.20 in "HP3070 Series 3 Users" Documentation, Hewlett Packard Co., Part Number E4000–13602.

* cited by examiner

*Primary Examiner*—Phung M. Chung

(57) ABSTRACT

A system for efficient utilization of multiple test systems may include an apparatus for testing an electronic circuit board, which comprises a number of computer readable media containing computer readable program code comprising code for a test analysis system that interfaces with at least two test systems. The test analysis system reads a description of said board's board topology and analyzes a number of potential defects of said board based on that description. The test analysis system creates at least two test procedures for the at least two test systems by creating a first test procedure to test the electronic circuit board on a first test system of the at least two test systems. The system then creates at least one other test procedure to test the electronic circuit board on at least one other test system of the at least two test systems. The system then optimizes the at least one other test procedure based on at least one other of the at least two test procedures created for the at least two test systems to reduce redundancies in the at least two test procedures.

16 Claims, 4 Drawing Sheets

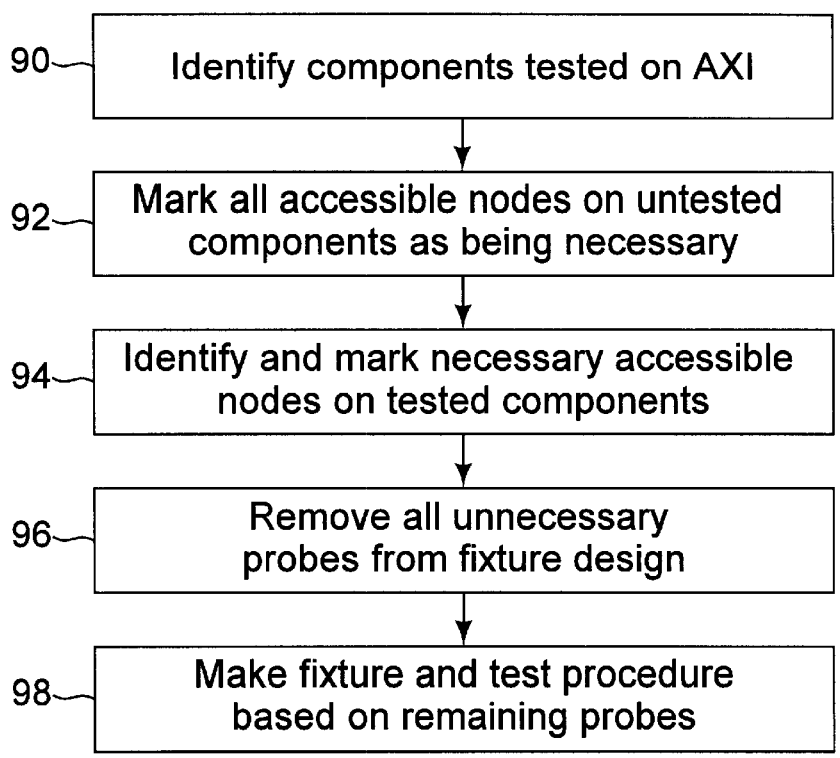
FIG. 5
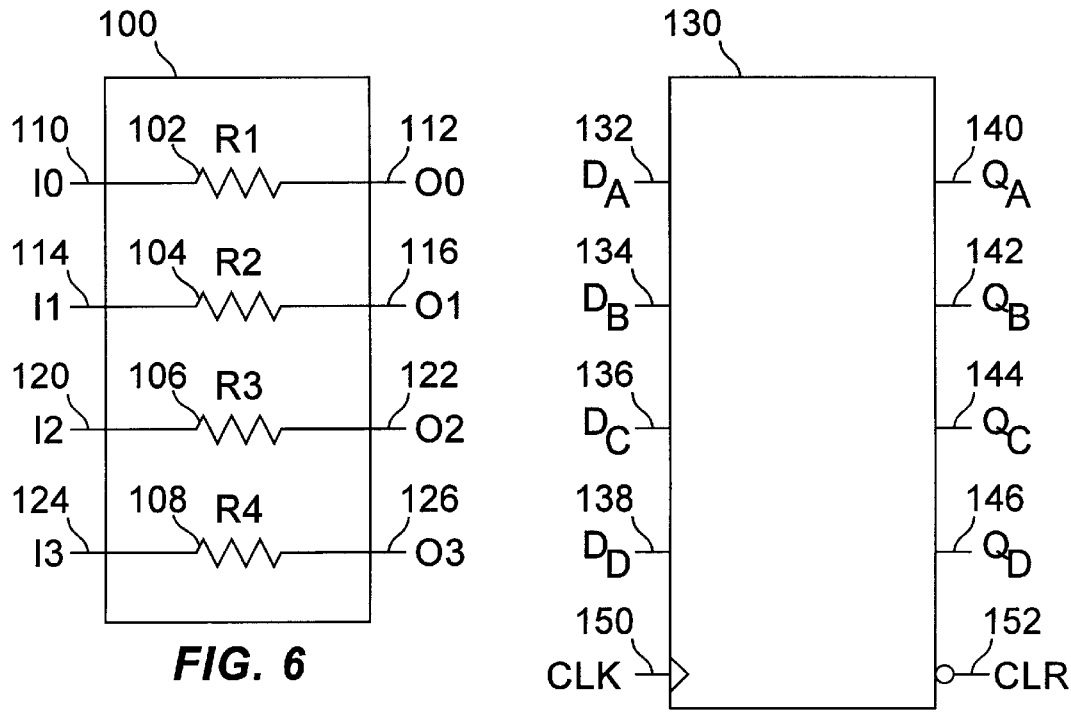
FIG. 6
FIG. 7

SYSTEM FOR EFFICIENT UTILIZATION OF MULTIPLE TEST SYSTEMS

FIELD OF THE INVENTION

This invention pertains to the field of testing electrical printed circuit boards, and more particularly, to a system for the efficient utilization of multiple test systems to test electrical printed circuit boards.

BACKGROUND OF THE INVENTION

Electrical printed circuit (PC) boards are typically manufactured in a complex, highly automated process. Multiple horizontal layers of metal electrical conductors, or traces, are sandwiched between insulating layers and interconnected with vertical connections known as vias. Electrical components, including passive electrical devices (such as resistors, capacitors, inductors, etc.) and active electrical devices (such as digital integrated circuits, A/D converters, operational amplifiers, etc.) may then be connected to the printed circuit board by soldering the components to pads on the surface of the PC board or into holes drilled through the board.

The completed PC boards must then be tested for a number of possible defects. This testing typically verifies that the traces, vias, and connectors in the blank PC board are acceptable and that the proper components are on the PC board in their correct locations, oriented correctly, and appropriately soldered in place. Some typical defects include:

Missing components: one or more required components are not present on the board;

Wrong components: one or more components are of incorrect value (e.g. 33K ohm resistor instead of a 3.3K ohm resistor), or are of incorrect type (e.g. a digital PCI controller is placed where a digital SCSI controller should be);

Open solder joints: one or more electrical connections between the PC board and a device on the board failed to solder properly so there exists no electrical connection between the PC board and one or more device pins;

Solder shorts: an undesirable electrical connection exists between two locations on the PC board due to an improper soldering process;

Insufficient solders: an unreliable electrical connection exists such that physical stresses such as those caused by dropping the board or exposing it to thermal extremes may possibly (over time) cause the joint to fail.

Testing the completed PC boards is a difficult process since many PC boards perform numerous functions and include a large number of components. Furthermore, many of the electrical conductors are buried inside the PC board, rendering a visual inspection (VI) impossible. Relying solely on functional tests, consisting of applying power and causing the PC board to perform all possible functions, is generally inefficient and wasteful for several reasons. Functional tests are slow since it takes time to cycle through all functions, the location of defects is not precisely identified, and if power is applied to a defective PC board many expensive components may be destroyed, compounding the defects. Therefore, since visual and functional tests are not generally sufficient, other specialized testing equipment may be used to test the PC board.

A variety of independent mechanisms may be employed to test the PC board for failures. Some of these techniques are:

Automated optical inspections (AOI): a computer-controlled system employing devices such as digital cameras, etc.;

Automated x-ray inspections (AXI): a computer-controlled x-ray system;

Electrical process test inspections: a computer-controlled measurement system (typically, but not limited to, a type of system referred to as an in-circuit test (ICT) system).

No inspection system can guarantee a high probability of detecting and locating all possible types of defects. Additionally, the problem is made worse by virtue of the fact that the probability of detection of defects by the various systems can be lessened by a number of factors such as the complexity of the circuitry on the PC board, the size of the PC board, and the quality of the individual tests employed to look for the defects. For this reason, manufacturers may employ several different types of test systems in the inspection process. By doing this, manufacturers hope to have a high probability of detection for all of their common defects.

In employing multiple systems, manufacturers have no means for analyzing the defect-detection capability of each system for each of the potential defects on a given PC board. Therefore, a significant amount of cost is incurred due to the inefficiency of employing two or more types of systems that are inspecting for the same defect. For example, if a manufacturer employs an automated optical inspection (AOI) system, an automated x-ray inspection (AXI) system, and an in-circuit test system (ICT) for a particular board, all three systems will spend considerable time and money looking for the same defects (e.g. solder opens, etc.). The expense of this process can be considerable due not only to the amount of time spent by the various systems in duplication of effort, but also in the costs associated with programming the systems, creating fixtures to connect the PC board to the test systems, maintenance and alignment of the systems, etc. As PC boards become more complex and components are increasingly miniaturized, fixtures become more costly, heavy, complex, and unreliable.

For example, an in-circuit tester includes a test bed for holding a completed PC board. The PC board is generally screwed down to the test bed to provide a good connection between the electrical ground on the PC board and the ground on the ICT. A two-dimensional array of electrical probes, or "bed of nails," must then be adapted to contact exposed electrical conductors on the PC board. A fixture must be designed and fabricated to provide this interface between the bed of nails and the PC board conductors, since the ICT nails are generally not in the correct location and are too widely spread to directly probe the PC board. A typical fixture consists of a flat insulating board with connectors on one side to connect with the nails extending from the ICT. Precisely positioned probes extend from the other side of the fixture to contact nodes on the PC board. (A node is a junction point within a network, such as the electrical connection between two or more component pins. Each node may have several probing locations, such as at the two or more component pins.) Extensive wiring is required in the fixture to connect each nail to the right probe. The design and fabrication of a fixture is a major and costly part of the test development process. As electronics become more widely used and more complex, testing difficulties are exacerbated, and a need to improve PC board testing methods and reduce the costs of designing and fabricating fixtures becomes more urgent.

A need therefore exists for a system to efficiently test electrical printed circuit boards on multiple test systems, reducing the redundancy of the tests and speeding them up while keeping a high probability of detecting defects. A further need exists to reduce the cost, complexity, size and weight of the fixtures needed to connect electrical printed circuit boards to the test systems.

SUMMARY

To assist in achieving the aforementioned needs, the inventors have devised a system for the efficient utilization of multiple test systems.

A method for developing a test procedure to test an electrical circuit board on multiple test systems having features of the present invention comprises: providing a description of an electrical circuit board having a plurality of elements connected thereto; identifying a subset of the plurality of elements on the electrical circuit board to be tested on a first test system, wherein the first test system is capable of testing the subset of the plurality of elements for defects; creating a first test process to test the subset of the plurality of elements on the first test system; storing the first test process on a medium readable by the first test system; identifying a remainder of the plurality of elements on the electrical circuit board to be tested on at least one other test system, wherein the at least one other test system is capable of testing the remainder of the plurality of elements for defects; creating at least one other test process to test said remainder of the plurality of elements on the at least one other test system; and storing said at least one other test process on at least one medium readable by the at least one other test system.

Also disclosed is a method for testing an electrical circuit board, comprising: providing a first test system; providing a second test system; connecting the first test system to the second test system so that data can be passed from the first test system to the second test system; connecting the electrical circuit board to said first test system; said first test system testing the electrical circuit board; if the first test system finds no defects on the electrical circuit board, said first test system passing data identifying the electrical circuit board to said second test system to indicate that the electrical circuit board has been tested and any defects found were repaired; connecting the electrical circuit board to said second test system; and if said second test system received data from said first test system indicating that the electrical circuit board connected to said second test system was tested on said first test system and no errors were found, said second test system testing the electrical circuit board.

Also disclosed is an apparatus for testing an electronic circuit board, which comprises a number of computer readable media containing computer readable program code comprising code for a test analysis system that interfaces with at least two test systems. The test analysis system reads a description of said board's board topology and analyzes a number of potential defects of said board based on that description. The test analysis system creates at least two test procedures for the at least two test systems by creating a first test procedure to test the electronic circuit board on a first test system of the at least two test systems. The system then creates at least one other test procedure to test the electronic circuit board on at least one other test system of the at least two test systems. The system then optimizes the at least one other test procedure based on at least one other of the at least two test procedures created for the at least two test systems to reduce redundancies in the at least two test procedures.

BRIEF DESCRIPTION OF THE DRAWING

An illustrative and presently preferred embodiment of the invention is illustrated in the drawing, in which:

FIG. 5 is a flow chart illustrating test optimization of a second test system based on the test procedure of a first test system;

FIG. 6 is a schematic of a resistor pack in a library file illustrating nodes eligible for probe removal strategies; and FIG. 7 is a schematic of a digital IC in a library file illustrating nodes eligible for probe removal strategies.

DESCRIPTION OF THE PREFERRED EMBODIMENT

Figure 1:
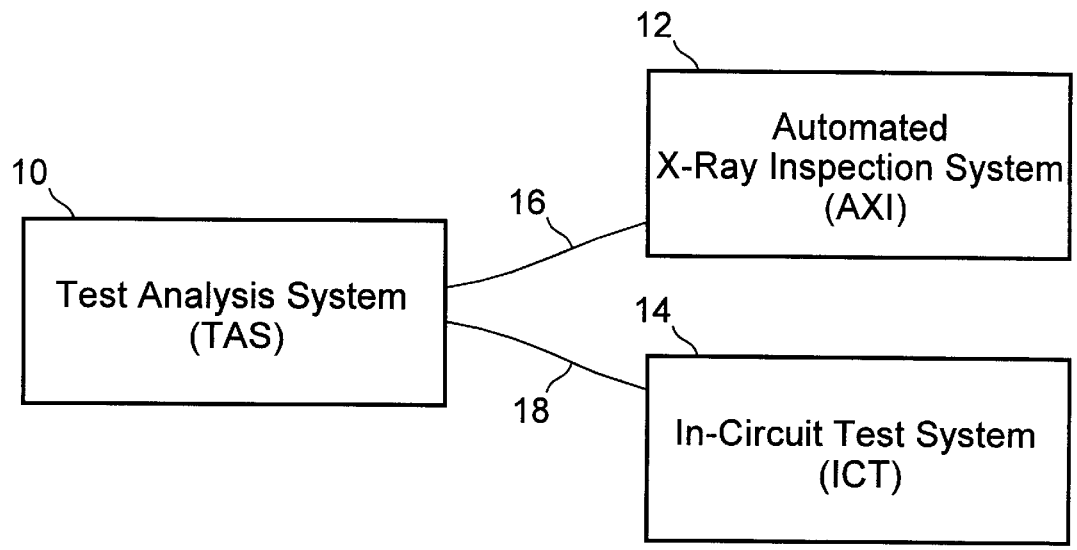
FIG. 1 is a block diagram of a test development system with multiple test systems.

Multiple test systems may be used to effectively test electrical printed circuit (PC) boards. However, the strengths and weaknesses of each type of test system frequently overlap. The following table lists the most common systems and, given the state of the art today, their ability to detect certain types of common defects:

|     | SOLDER OPENS | SOLDER SHORTS | MISSING COMP. | COMP. WRONG TYPE | COMP. WRONG VALUE | INSUFF. SOLDER |
| --- | --- | --- | --- | --- | --- | --- |
| VI  | LOW | LOW | MEDIUM | LOW | LOW | LOW |
| AOI | MEDIUM | MEDIUM | HIGH | LOW | LOW | MEDIUM |
| AXI | HIGH | HIGH | HIGH | LOW | LOW | HIGH |
| ICT | MEDIUM | HIGH | HIGH | HIGH | HIGH | LOW |

A system for efficient utilization of multiple test systems enables manufacturers to exploit the strengths of their test systems and minimize test redundancies. For example, in an exemplary preferred embodiment, an automated x-ray inspection (AXI) test system may be used to test for short circuits, open circuits, missing components, and insufficient solder. An in-circuit test (ICT) system may be used to probe exposed electrical connections on a completed PC boards to also test for shorts and opens, and also for defective electrical components or components with the wrong value or type. The elements tested on a PC board may include traces, vias, and connections of the board, the electrical components attached to the board, and the connections between them, etc.

To test an electrical printed circuit board, a test process is first developed for each test system used, e.g. for the AXI system and the ICT system. Additionally, for test systems requiring a fixture to connect the PC board to the test system, a fixture is designed and fabricated during the test development process.

Once the test process has been developed and stored for each test system, and the required fixtures have been designed and fabricated, multiple PC boards may be tested during the manufacturing process on each test system according to the developed test procedure. Generally, each PC board is first tested on the test system which can most easily detect gross errors without causing additional damage to a defective PC board. For example, a visual inspection (VI) or automated optical inspection (AOI) may be used to determine that all the components have been connected in the proper locations and oriented correctly. An automated x-ray inspection (AXI) test system may be used to test for short circuits before applying power to the PC board, which could destroy multiple sensitive electrical components. The test process may then proceed to more invasive tests, such as the in-circuit test (ICT) which probes exposed electrical conductors and passes test currents between probes.

The in-circuit test may be performed in two stages: a first stage in which the board is unpowered and passive electrical components are tested, and a second stage in which the board is powered to test active electrical components such as digital integrated circuits. (A test with either no power applied to the board or with power insufficient to make a component operate as intended, i.e., applying 2 volts to a 5 volt power terminal, is within the scope of an "unpowered" test.) For example, during the unpowered stage, two probes could be used to test a resistor on a PC board by connecting with each of the two terminals of the resistor and passing a test current through the resistor. Thus, the placement and connection of the resistor can be tested, and the resistance can be measured to ensure that the correct resistor was attached, without applying power to the entire board. During the second stage, power may be applied to the entire board to allow testing of individual active components which must be powered and operating to test.

Finally, various functional tests may be used, also applying power to the entire board to test its various functions at a system level or to test groups of components, in contrast to the individual component tests of an in-circuit test.

A test process may include multiple test systems, progressing from less invasive and potentially damaging tests to full functional tests, depending upon the requirements of the manufacturer. The acceptable cost limits the number of test systems used, as they are generally very expensive. Complex PC boards may require a more cautious and thorough testing process which includes several test systems, while simple, inexpensive PC boards may not justify the cost of multiple test systems.

A system for efficient utilization of multiple test systems greatly reduces the time required to test a PC board during the manufacturing process. As a result, more PC boards can be tested on the test systems and the relative cost of the test systems is lowered. The cost and complexity of fixtures is also greatly reduced, resulting in faster fixture fabrication times.

A test development process according to a preferred embodiment of the system for efficient utilization of multiple test systems is shown in block diagram form in FIG. 1. In this exemplary embodiment, a test may be developed to test a PC board on an x-ray inspection test system and an in-circuit test system. A test analysis system 10 (TAS) is connected to and interfaced with an AXI test system 12, such as a Hewlett-Packard 5DX®, and an ICT test system 14, such as a Hewlett-Packard 3070. The TAS 10 is preferably connected to the AXI 12 and the ICT 14 with a TCP/IP network 16 and 18. Generally, the TAS 10 comprises a computer capable of interfacing with the test generation hardware of the test systems 12 and 14. In most test systems, the test generation hardware also comprises a computer. TAS software required to develop an efficient test process is distributed across the TAS 10, the ICT 14, and the AXI 12.

Figure 3:
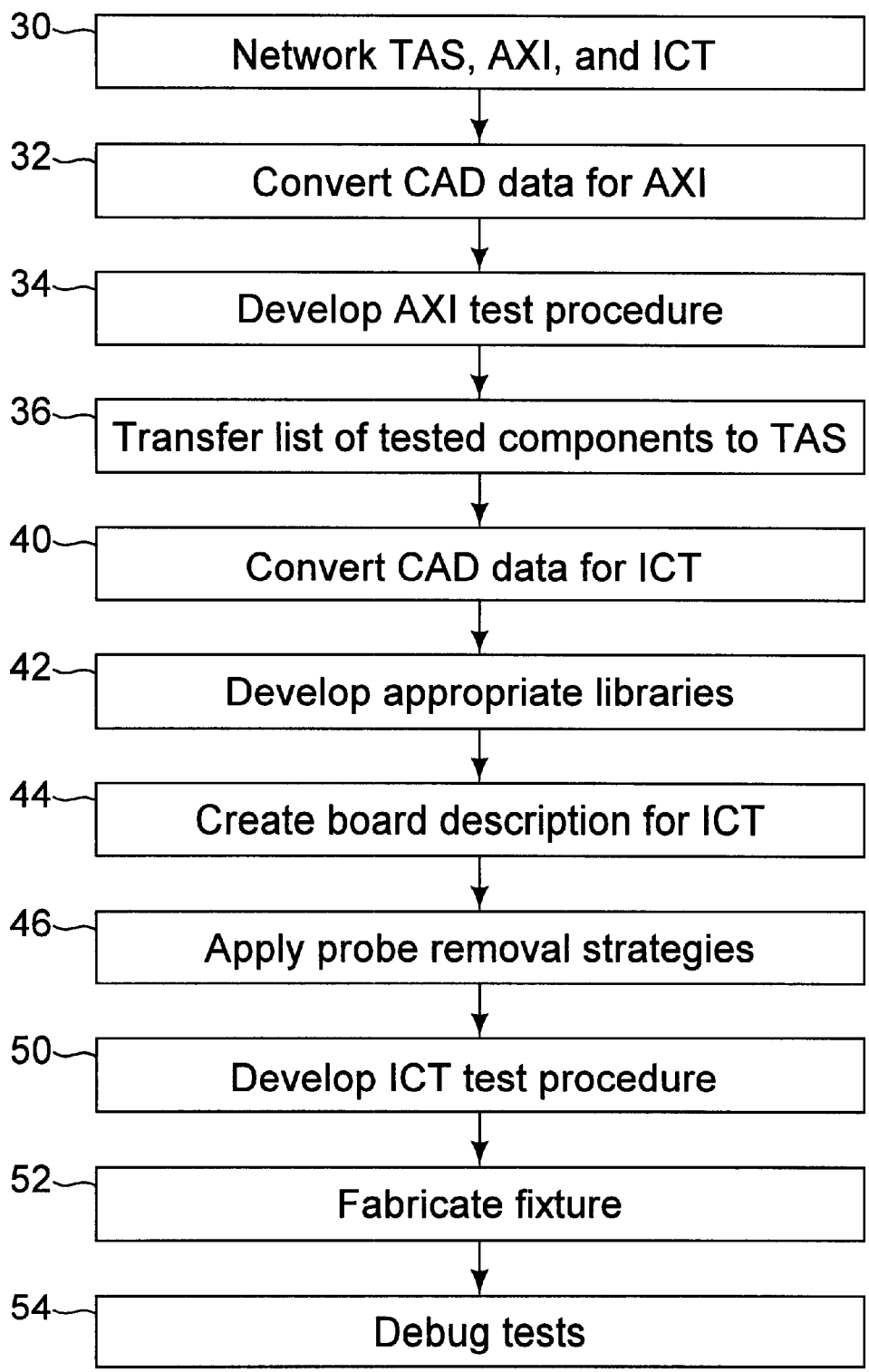
FIG. 3 is a flow chart of a test development process.
Figure 4:
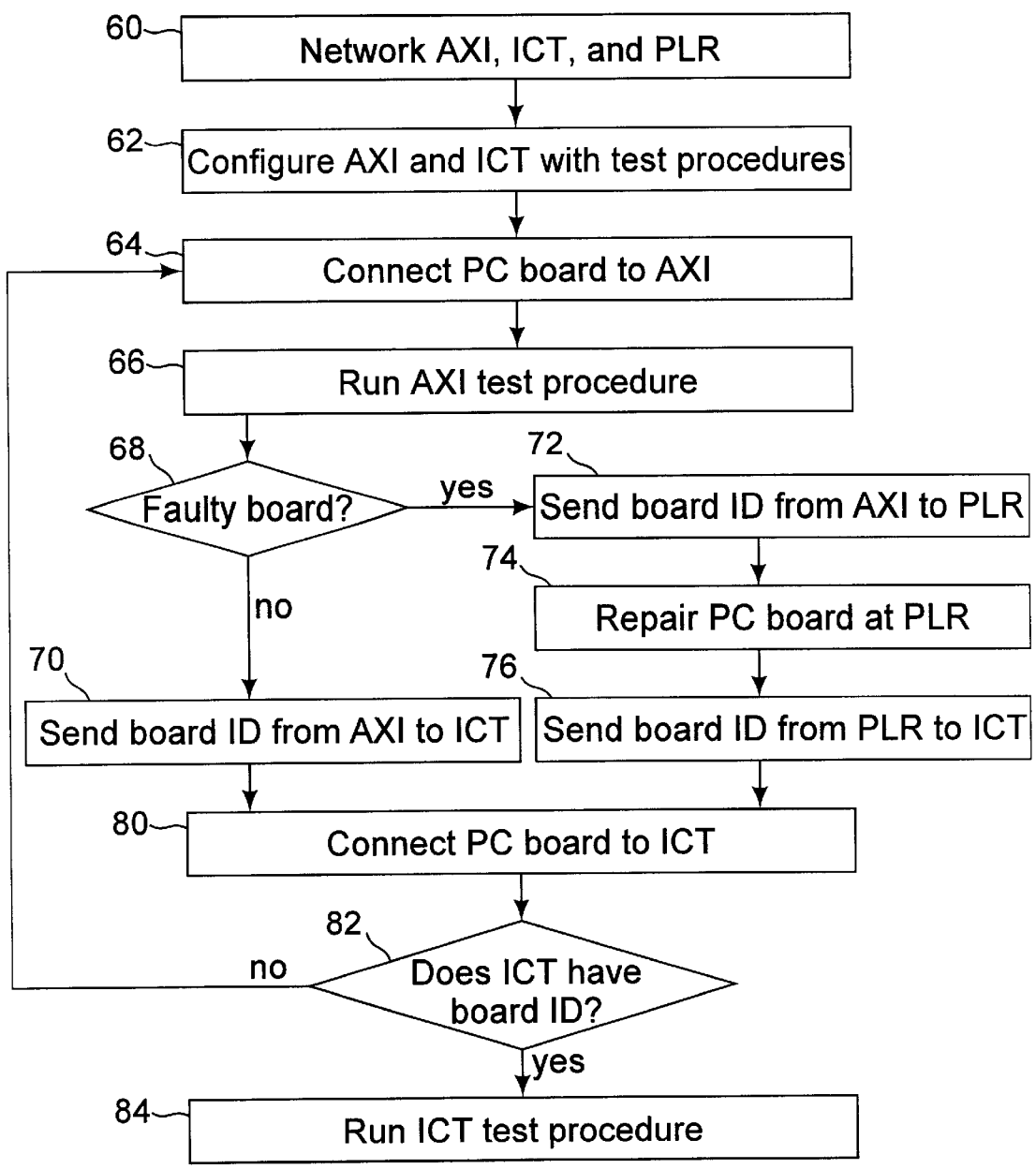
FIG. 4 is a flow chart of a PC board test process.

The test development process for efficient utilization of multiple test systems is shown in flow chart form in FIG. 3. The TAS 10, the ICT 14 and the AXI 12 are networked 30 to allow them to exchange information during the test development process. In a preferred embodiment, they are connected across a TCP/IP network. CAD data describing the PC board and its topology are then fed into the first test system, the AXI 12, and the CAD data are converted 32 in the AXI 12 to a format required by the AXI 12. In an alternate embodiment, if the test systems are not available during the test development process, an external computer such as the TAS 10 may be programmed to perform all the steps otherwise performed by the test systems, such as converting 32 the CAD data to test system format and developing the test.

The test procedure for the first test system 12 is then developed 34. This involves examining the board architecture and components to determine which elements can be effectively tested by x-ray, thereby analyzing the potential defects on the board. For example, solder joints and component placement may generally be effectively tested by x-ray inspection.

A file containing a list of the components or elements tested by the AXI test procedure is then transferred 36 to the TAS 10. In a preferred embodiment, the tested components file created by the AXI 20 is a text file with one component name (i.e. C34, U12) per line. The tested components file allows optimization of later test procedures. Sending a list of components tested is equivalent to sending a list of tests performed by the AXI 20, since the TAS 10 system is configured to be aware of what tests the AXI 20 performs on each component.

The CAD data describing the board are fed into the second test system, the ICT 14, and the CAD data are converted 40 into ICT format. The converted CAD data describe the board topology for the ICT, such as the location of components and how they are connected to each other, indicating where probes may contact the board to apply and receive test currents.

Libraries describing some of the components on the board may then be developed 42, enabling the ICT 14 to probe and test the components. For example, and as will be discussed in greater detail hereinafter, a resistor pack may include a number of discrete resistors in one package having numerous connection pins. If the resistor pack is included on the board, the converted CAD data will include the location and type of the resistor pack. The library file will include details about the resistor pack such as resistor values, allowing the ICT 14 to probe and test the resistor pack on the PC board. Library files are created for components such as resistor packs to describe the contents of the pack, and for digital integrated circuits to describe how to test them, since integrated circuits must be powered and have their inputs manipulated to test them.

A board description is then created 44 from the converted CAD data and library files. In one embodiment, Hewlett Packard Board Consultant software is used to create files, including "board.o" and "board.xy.o", from which a fixture and test procedure may be developed. These files enable placement of ICT probes on all exposed electrical conductors on the PC board. The file "board.o" contains a list of components and describes the electrical connections between each pin. The file "board.xy.o" describes access limitations on the board, or nodes on the board which cannot be accessed by fixture probes, as well as locations where probes have access. Nodes may be inaccessible for a number of reasons, such as being buried in an inner layer of the board, being covered by a component on top, or being too close to another node to allow a probe access. Note that each node may have several probing locations available, and all must be inaccessible for the node to be inaccessible.

The TAS 10 software can then apply probe removal strategies 46 to reduce or eliminate redundancy in the overall test process and simplify the ICT fixture. For example, as will be discussed in greater detail hereinafter, if a component will be tested by the AXI 12, it will appear in the list transferred 36 from the AXI 12. If the test applied by the AXI 12 is sufficient, the component test may be simplified in the test procedure for the ICT 14, reducing testing time and reducing the number of probes required, thereby simplifying the ICT fixture. It is important to note that some tests performed on a given component by earlier test systems may not reveal enough information to allow complete removal from the test procedure in later test systems. An x-ray inspection of a component has a high probability of detecting shorts or opens on the solder connections, but has a low probability of detecting whether the component has the correct part value, such as the value of a resistor, so a later test system should generally still test the component value. The tests for each component may also be simplified by the TAS 10 software. For example, if the library file for a resistor pack indicates that multiple resistors are contained in the pack, the test may be optimized by including only enough probes in the fixture to test one resistor in the resistor pack, thereby testing for correct placement of the pack and connection of the tested resistor, as well as the value of the resistor pack, leaving the test for solder connections on the remaining pins to the AXI test system 12.

Some redundancy in the testing may be desirable to either increase probability of defect detection or to provide statistical data verifying the detection of certain defects by previous test systems.

In a preferred embodiment, the test development process allows a great deal of user control, allowing the test designer to choose whether to redundantly test some components or not to test other components at all. In this embodiment, the TAS 10 applies the probe removal strategies to provide a suggested efficient test procedure, but may be overridden by the user during the test development process.

After the probe removal strategies have been applied 46, an ICT test procedure is developed 50. For example, a procedure to control which electrical conductors or nodes will be probed, and in what order, is developed. The procedure typically includes a description of the test current and voltage levels to be applied through the input probe(s) and what current and voltage levels to expect on the output probe(s). The fixtures to connect the PC boards to the ICT test system 14 are fabricated 52, and the test procedure is debugged 54 using a board which is known not to have defects. The resulting test procedure and fixtures may be used to test a stream of PC boards during the manufacturing process.

Figure 2:
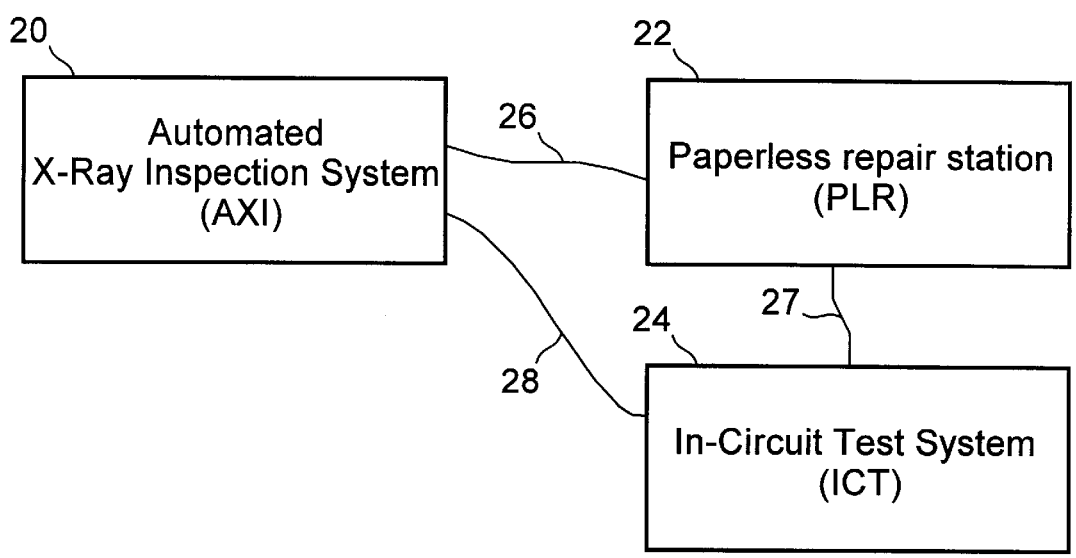
FIG. 2 is a block diagram of a test network with multiple test systems.

In an alternative embodiment of the test development process, depending upon the capabilities of the computers embedded in each test system 12 and 14, the AXI 12 and the ICT 14 may be directly connected and interfaced as illustrated in FIG. 2, and the test development software may be distributed across the AXI 12 and the ICT 14, without an external TAS computer 10. In this embodiment, the TAS software is executed on the AXI 12 and the ICT 14 to optimize the test process as discussed above.

For example, the test development steps for each test system may be performed on the appropriate test system, and the test optimization may be performed on one or more of the test systems. In the exemplary embodiment discussed herein comprising an AXI 12 and an ICT 14, the AXI test development, including selection of elements to test, would be performed on the AXI 12. The AXI 12 would transfer the list of elements or components it tests directly to the ICT 14, then probe removal strategies would be applied and ICT test development would be performed on the ICT 14.

It is important to note that the specific type of test systems (e.g., 12 and 14) included in the system for efficient utilization of multiple test systems is exemplary in nature, and may be adapted or added to depending upon the test requirements. Furthermore, the decision of whether to include a TAS computer 10 depends upon the capabilities and limitations of the test systems used and the needs of the manufacturer. However, the inventive concepts disclosed herein are applicable to the various combinations of test systems, whether known currently or developed in the future. For example, other test configurations may require an AOI test system and an ICT test system, while another may require an AOI test system, an AXI test system and an ICT test system.

A manufacturing test process according to an exemplary preferred embodiment of the system for efficient utilization of multiple test systems is shown in block diagram form in FIG. 2. An AXI 20 test system and an ICT 24 test system are networked 60 together, preferably by a TCP/IP network 28. A paperless repair station (PLR) 22 is also networked between the AXI 20 and the ICT 24 on networks 26 and 27. A paperless repair station may be connected to a test system to receive defect reports directly from the test system. An operator at the PLR may then repair defective PC boards without referring to the test system or printouts of defects.

The AXI 20 and the ICT 24 are then configured 62 with the test procedures developed previously. Once the connection and configuration is complete, a series of PC boards can be tested on the system, with the testers running in parallel as the stream of boards moves through the system.

A PC board is first connected 64 to the AXI 20, and the AXI test procedure is run 66 to test a subset of the elements or components on the board for shorts, opens, missing components, etc., as determined during the test development process.

If a fault is detected in the PC board 68, the PC board identifier (board ID) is sent 72 from the AXI 20 to the PLR 22, preferably along with a description of the defect. An operator at the PLR 22 can then repair 74 the PC board, and the PLR station 22 sends 76 the board ID to the ICT 24. Alternatively, a manufacturing test process may exclude the PLR 22. In this case, an operator monitors the AXI 20 to learn of defects and would either manually send the board ID to the ICT 24 after repair or could retest the PC board on the AXI 20, allowing it to transmit the board ID to the ICT 24.

It is also within the scope of this invention, however, to send an unrepaired PC board to subsequent test systems, either by sending the PC board identifier on despite defects, or by overriding the check of PC board identifiers in later test systems. One reason for sending unrepaired PC boards on to subsequent test systems is to verify test results or to gather statistical data about the probability of the test systems to detect given defects.

If no faults are detected in the PC board 68 by the AXI 20, the AXI 20 sends 70 the board ID to the ICT 24 across the network 28, indicating to the ICT 24 that the board was tested, no defects were found, and the board is ready for the ICT 24 to test it. The PC board identifier in the preferred embodiment comprises a serial number which may either be manually entered on the AXI 20 by the test operator or which may be scanned in automatically by the AXI 20 by a bar code reader or other method. The PC board identifier may be transferred to the ICT 24 individually in a file by itself, or may be collected in a file with other PC board identifiers to be transferred to the ICT 24 in a larger batch, as best suits the needs of the manufacturing process. In the preferred embodiment, variables in the AXI 20 are configured to contain the name of a directory in the ICT 24 computer and the network location of the ICT 24 computer. As each board is successfully tested, the AXI 20 creates a file named with the serial number of the board and transfers it to the directory in the ICT 24 computer. Similarly, as each defective board is repaired at the PLR 22, the PLR 22 creates a file named with the serial number of the board and transfers it to the directory in the ICT 24 computer.

The PC board is then connected 80 to the ICT 24 and the PC board identifier of the board is either manually entered or automatically detected, as stated above. The PC board identifier is checked 82 against the list of PC boards successfully tested on the AXI 20 or repaired at the PLR 22. If the PC board identifier of the board under test is not in the list, the board is returned 64 to the AXI 20 to be tested. If the PC board identifier is in the list, the ICT test procedure is run 84 on the board according to the test procedure created during the test development process. The process of test, repair, and advancement to a subsequent test system such as functional test systems, followed by other stages of manufacturing such as assembly in a housing, may then continue according to the needs of the manufacturer.

As stated previously, the test process may be run as continuous process, with PC boards being moved in a stream through the AXI 20 and the ICT 24, with both operating simultaneously, or batches of PC boards may be tested on the AXI 20 before being moved to the ICT 24.

The testing process is greatly benefitted by networking the test systems and transferring the PC board identifiers in order to prevent invasive testing of boards before less invasive tests have been run first. As a result, hazardous defects detected on earlier systems can be repaired before power is applied by later test systems, preventing damage to expensive sensitive electrical components.

The duration of the testing process and cost of fixtures is also greatly reduced by optimizing the test procedure. The strengths of each test system can thus be focused on, reducing redundant tests and selecting only tests with a high probability of detecting defects.

The TAS software greatly aids the test designer to optimize the test procedure. As discussed above, the TAS software may be distributed among the test systems and external computers as desired, and among various programs according to the test systems selected. In one preferred embodiment, the TAS software is distributed across a Hewlett-Packard 5DX® AXI test system, a Hewlett-Packard 3070 ICT test system, and one or more computers with a UNIX® operating system, and is located in various programs in the system, such as the Hewlett Packard Access Consultant program used to remove probes during fixture development for the ICT test system. Operation of the "Board Consultant" and "Access Consultant" programs is described in "Test Development Tools, Chapter 2 - HP Board Consultant", pp. 2.1–2.32 and "Test Methods: Limited Access, HP Access Consultant", pp. 2.1–2.20 in *HP3070 Series 3 Users' Documentation*, Hewlett Packard Co., Part Number E4000-13602, which is incorporated herein by reference for all that it discloses. As stated above, the embodiment which distributes the TAS software across the various test systems and which employs the computer hardware of the test systems is preferred but is not exclusive. An alternative embodiment may concentrate the TAS software all in an external computer without including software embedded on the test systems.

The TAS software comprises the test system dependent software required to convert PC board CAD descriptions into test system formats and to develop test procedures for each test system. An important function of the TAS software of a preferred embodiment is to optimize the test procedures. Generally, a test is developed for the first test system based on optimizations known by the TAS, or provided to it, then an optimized test is developed for the second test system, removing redundant tests from the test procedure for the second test system. For example, when an ICT 24 requiring a fixture is used after an AXI 20, the TAS software removes probes for redundant component tests or tests with low probability of defect detection, as directed by the test designer. Probe removal involves making a list of all accessible nodes which could be probed, identifying a subset of the accessible nodes as necessary for testing, then removing the unnecessary probes from the list to optimize the test and fixture.

The TAS software is configured to be aware of which test systems are included and the order of the test systems in the process flow, as well as the capabilities of each test system. Based on this information, the TAS software optimizes the test procedures. The nature of the optimization depends upon the capabilities and order of the test systems. Referring now primarily to FIG. 5, for the exemplary preferred embodiment discussed herein which includes an AXI 20 and an ICT 24, the TAS software first identifies the components to be tested on the AXI 20 by examining the tested components file prepared by the AXI 20. Next, all accessible nodes connected to previously untested components are marked 92 as necessary for the ICT 24 test.

The components tested on the AXI 20 are tested for correct solder joints, placement and orientation, but must then be tested on the ICT 24 to check for defective components or improper component values. Therefore some nodes on previously tested components must be identified and marked 94 as necessary for the ICT 24 test. Various probe removal strategies may be applied to determine which probes are necessary on previously tested components, based upon the capabilities and test order of the test systems.

For example, for "multipack" components, that is, components having more than one functional unit packaged together, it may be desirable to test only one of the functional units in the component to verify the component value and operation. The resistor pack 100 shown in FIG. 6 is a multipack component in which multiple resistors R1 102, R2 104, and R3 106 are included in the same housing. A library file is created for the ICT 24 describing the resistor pack 100. The solder connections between the PC board and all the nodes on the pack 100 are tested by the x-ray inspection on the AXI 20. This includes the inputs I0 110, I1 114, I2 120, and I3 124, and the outputs O0 112, O1 116, O2 122, and O3 126. To test for the proper component value, only one resistor needs to be tested on the ICT 24. To test the value of resistor R1 102, as shown in FIG. 6, the nodes connected to I0 110 and O0 112 must be probed, so those two probes are marked 94 as necessary. The remaining probes on nodes connected to I1 114, I2 120, I3 124, O1 116, O2 122, and O3 126 may be removed unless they are marked as necessary to test another component. Besides testing the resistor pack for the proper value, the optimized test checks for proper operation of the pack, based on the assumption that if one resistor in the pack operates, they all do.

The number of probes required may be further reduced if nodes were previously marked as necessary on the part for a different component test. In this case, by selecting to probe the resistor in the resistor pack which connects to the previously marked node, nodes which are necessary for two separate component tests may be shared. For example, if a previous component test required a probe on the node connected to the input I2 120 of resistor R3 106, then resistor R3 106 should be selected as the resistor to test in the pack, and the node connected to the output O2 122 should be marked as necessary.

In another example, a library file is created for a digital IC such as a four bit register shown in FIG. 7. The four bit register contains four separate 1-bit register units. Of the four bits, only one needs to be tested in the IC after the AXI tests all the solder connections. To test one bit, four nodes must be probed, a data input $D_A$ 132, a data output $Q_A$ 140, the clock CLK 150, and the clear CLR 152. The remaining nodes for $D_B$ 134, $D_C$ 136, $D_D$ 138, $Q_B$ 142, $Q_C$ 144, and $Q_D$ 146 do not need to be probed.

After appropriate probe removal strategies are performed, such as the strategy described above based on the library file, all unnecessary probes are removed 96 from the fixture design. A fixture can then be made 98 and a test procedure developed for the ICT 24 based on the remaining probes.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A method for developing a test procedure to test an electrical circuit board on multiple test systems, comprising:
   providing a description of an electrical circuit board having a plurality of elements connected thereto;
   identifying from the description of the electrical circuit board a subset of the plurality of elements connected to the electrical circuit board to be tested on a first test system, wherein the first test system is capable of testing the subset of the plurality of elements for defects;
   creating a first test process to test said subset of the plurality of elements on the first test system;
   storing said first test process on a medium readable by the first test system;
   identifying from the description of the electrical circuit board a remainder of the plurality of elements on the electrical circuit board to be tested on at least one other test system, wherein the at least one other test system is capable of testing the remainder of the plurality of elements for defects;
   creating at least one other test process to test said remainder of the plurality of elements on the at least one other test system; and
   storing said at least one other test process on at least one medium readable by the at least one other test system.

2. The method of claim 1, wherein the first test system performs a first type of test and the at least one other test system performs at least one second type of test, the method further comprising retesting a portion of the subset of the plurality of elements on the at least one other test system.

3. The method of claim 1, wherein said identifications are performed interactively with a test analysis system.

4. The method of claim 1, wherein said process creations are performed interactively with a test analysis system.

5. A method for testing an electrical circuit board, comprising:
   providing a first test system;
   providing a second test system;
   connecting said first test system to said second test system so that data can be passed from said first test system to said second test system;
   connecting the electrical circuit board to said first test system;
   said first test system testing the electrical circuit board;
   if the first test system finds no defects on the electrical circuit board, said first test system passing data identifying the electrical circuit board to said second test system to indicate that the electrical circuit board may be tested by said second test system;
   connecting the electrical circuit board to said second test system; and
   if said second test system received data identifying the electrical circuit board connected to said second test system indicating that the electrical circuit board may be tested by said second test system, said second test system testing the electrical circuit board.

6. The method of claim 5, further comprising:
   if the first test system finds a defect on the electrical circuit board, said first test system passing data identifying the electrical circuit board to a repair station to indicate that the electrical circuit board has been tested and is defective;
   repairing the electrical circuit board at the repair station; and
   the repair station passing data identifying the electrical circuit board to said second test system to indicate that the electrical circuit board may be tested by said second test system.

7. The method of claim 5, wherein connecting said first test system to said second test system comprises:
   connecting an electrical cable between said first test system and said second test system; and
   establishing a TCP/IP network connection across the electrical cable between said first test system and said second test system.

8. The method of claim 5, wherein said first test system testing the electrical circuit board comprises inspecting the electrical circuit board with x-rays.

9. The method of claim 5, wherein said second test system testing the electrical circuit board comprises placing a plurality of test probes against the electrical circuit board and passing an electrical test current through one or more of the plurality of test probes.

10. An apparatus for developing a test for an electronic circuit board, comprising:
   a. a number of computer readable media;
   b. computer readable program code stored on said number of computer readable media, said computer readable program code comprising code for a test analysis system that cooperates with at least two test systems, said test analysis system:

i. reading a description of said board's board topology;
ii. analyzing a number of potential defects of the electronic circuit board based on said description;
iii. creating at least two test procedures for the at least two test systems by:
   (1) creating a first test procedure to test the electronic circuit board on a first test system of the at least two test systems;
   (2) creating at least one other test procedure to test the electronic circuit board on at least one other test system of the at least two test systems; and
   (3) optimizing the at least one other test procedure based on at least one other of the at least two test procedures created for the at least two test systems to remove tests for previously tested potential defects and reduce redundancies in the at least two test procedures.

11. An apparatus as in claim 10, wherein the computer readable media for the test analysis system resides in the at least two test systems.

12. An apparatus as in claim 10, wherein the computer readable media for the test analysis system resides in a computer.

13. An apparatus as in claim 10, additionally comprising program code for instructing a given one of the at least two test systems to inspect for a previously tested potential defect of said number of potential defects, said given one of said at least two test systems being a different test system than a test system used to test said previously tested potential defect.

14. An apparatus as in claim 10, wherein a given one of the at least two test systems comprises an in-circuit test system, and wherein the program code for optimizing the at least one other test procedure for the in-circuit test system comprises code for:
   a. creating a list of accessible nodes to be probed on the electronic circuit board;
   b. identifying all accessible nodes connected to previously untested components on the electronic circuit board;
   c. identifying previously tested components which have at least one remaining potential defect not tested for in a previous test;
   d. identifying a minimum number of nodes connected to the previously tested components needed to test for the at least one remaining potential defect not tested for in a previous test;
   e. removing all unidentified nodes from the list of accessible nodes to be probed; and
   f. adjusting the at least one other test procedure to probe the nodes remaining in the list of accessible nodes to be probed.

15. An apparatus as in claim 14, wherein the code for identifying the minimum number of nodes connected to the subset of the number of previously tested components needed to test for the at least one remaining potential defect comprises:
   a. identifying multipack components having a plurality of functional units from among the previously tested components;
   b. selecting one of the plurality of functional units to test in each of the multipack components; and
   c. identifying all nodes necessary to test the selected one of the plurality of functional units as needed.

16. An apparatus as in claim 14, wherein the code for identifying the minimum number of nodes connected to the subset of the number of previously tested components needed to test for the at least one remaining potential defect comprises:
   a. identifying digital integrated circuits from among the previously tested components; and
   b. identifying all nodes necessary to test each digital integrated circuit.

* * * * *